US006894080B2

(12) United States Patent
Seiki et al.

(10) Patent No.: US 6,894,080 B2
(45) Date of Patent: May 17, 2005

(54) METHOD OF MANUFACTURING METHANOL

(75) Inventors: Yoshio Seiki, Hiroshima-ken (JP); Tetsuya Imai, Hiroshima-ken (JP); Kazuto Kobayashi, Hiroshima-ken (JP); Hiroyuki Osora, Hiroshima-ken (JP); Chie Kuwada, Hiroshima-ken (JP); Kazuhiro Morita, Tokyo (JP); Shuichi Miyamoto, Tokyo (JP)

(73) Assignees: Mitsubishi Heavy Industries, Ltd., Tokyo (JP); Mitsubishi Gas Chemical Company, Inc., Tokyo (JP)

( * ) Notice: Subject to any disclaimer, the term of this patent is extended or adjusted under 35 U.S.C. 154(b) by 215 days.

(21) Appl. No.: 10/197,516

(22) Filed: Jul. 18, 2002

(65) Prior Publication Data
US 2003/0032844 A1 Feb. 13, 2003

(30) Foreign Application Priority Data
Jul. 19, 2001 (JP) .......................... 2001-219931

(51) Int. Cl.$^7$ ............................................. C07C 27/00
(52) U.S. Cl. ...................... 518/700; 518/702; 518/704
(58) Field of Search ............................... 518/700, 702, 518/704

(56) References Cited
U.S. PATENT DOCUMENTS
6,218,439 B1    4/2001    Kobayashi et al.

FOREIGN PATENT DOCUMENTS

| EP | 1 008 577 | 6/2000 |
|----|-----------|--------|
| GB | 2 213 817 | 8/1989 |
| JP | 1-180841  | 7/1989 |

OTHER PUBLICATIONS

U.S. Appl. No. 10/197,423, filing date Jul. 18, 2002, Seiki et al.*
U.S. Appl. No. 10/197,519, filing date Jul. 18, 2002, Seiki et al.*

* cited by examiner

*Primary Examiner*—J. Parsa
(74) *Attorney, Agent, or Firm*—Oblon, Spivak, McClelland, Maier & Neustadt, P.C.

(57) ABSTRACT

A method of manufacturing methanol comprises producing a synthesis gas, recovering carbon dioxide from combustion exhaust gas by a carbon dioxide recovery apparatus provided with a carbon dioxide absorption tower and a carbon dioxide-absorbing solution regenerating tower, feeding the carbon dioxide to the upstream side and/or the downstream side of a reformer, allowing reaction of the synthesis gas to produce a reaction product, recovering a liquid crude methanol, and distilling the liquid crude methanol in a distillation apparatus provided with a topping tower, a pressure distillation tower and an atmospheric distillation tower to isolate refined methanol. Bottom liquid of the topping tower is heated and introduced into the pressure distillation tower, and the heat of distilled liquid discharged from this tower is utilized as a heat source for the regenerating tower and as a heat source for the atmospheric distillation tower.

9 Claims, 2 Drawing Sheets

METHOD OF MANUFACTURING METHANOL

CROSS-REFERENCE TO RELATED APPLICATIONS

This application is based upon and claims the benefit of priority from the prior Japanese Patent Application No. 2001-219931, filed Jul. 19, 2001, the entire contents of which are incorporated herein by reference.

BACKGROUND OF THE INVENTION

1. Field of the Invention

This invention relates to a method of manufacturing methanol.

2. Description of the Related Art

Jpn. Pat. Appln. KOKAI Publication No. 1-180841 discloses a method of manufacturing methanol ($CH_3$—OH) from hydrocarbon such as natural gas. Specifically, this publication describes a method of manufacturing methanol, which comprises:

reacting a gaseous hydrocarbon or a vaporized liquid hydrocarbon, by making use of a reformer, with water vapor in the presence of a nickel catalyst at a temperature ranging from 800 to 1000° C. to produce a synthesis gas comprising, as main components, hydrogen ($H_2$), carbon monoxide (CO) and carbon dioxide ($CO_2$);

allowing reaction of the synthesis gas to take place over a copper-based methanol-synthesizing catalyst which is placed inside a synthesis reactor at a pressure of 50 to 150 atm and at a temperature of 200 to 300° C. to produce a reaction product;

cooling the crude methanol;

separating the cooled crude methanol into unreacted gas and liquid crude methanol; and distilling the liquid crude methanol in one or more distillation columns to separate refined methanol and a waste water containing organic compounds having a lower boiling point than that of methanol (hereinafter, referred to as low boiling point organic compounds), another organic compounds having a higher boiling point than that of organic acid and methanol (hereinafter, referred to as high boiling point organic compounds).

In the aforementioned synthesis gas-producing step, by making use of a carbon dioxide recovery apparatus, carbon dioxide is recovered from a combustion exhaust gas which has been discharged from the reformer, and the carbon dioxide thus recovered is fed to the upstream side of the reformer and/or the downstream side of the reformer to obtain a synthesis gas having a desired molar ratio of $H_2/(CO+CO_2)$ which is suitable for the manufacture of methanol.

However, as the quantity of carbon dioxide to be recovered by the carbon dioxide recovery apparatus is increased in the conventional method of manufacturing methanol, the heat quantity required to be used in the carbon dioxide recovery apparatus is caused to increase correspondingly, thus inviting a shortage of heating sources and hence increasing the manufacturing cost of methanol.

BRIEF SUMMARY OF THE INVENTION

An object of the present invention is to provide a method of manufacturing methanol, which is capable of producing, by making use of a reformer, a synthesis gas having a suitable molar ratio of $H_2/(CO+CO_2)$ for the synthesis of methanol, and capable of making the most of heat of distilled liquid which has been recovered by a pressure distillation tower of distillation apparatus for using it as a heat source for the carbon dioxide recovery apparatus, thereby making it possible to cope with any increase in heat quantity to be used in the carbon dioxide recovery apparatus.

According to the present invention, there is provided a method of manufacturing methanol comprising:

reacting hydrocarbons with water vapor (steam) in a reformer to produce a synthesis gas containing hydrogen, carbon monoxide and carbon dioxide;

recovering carbon dioxide from combustion exhaust gas which has been discharged from the reformer by a carbon dioxide recovery apparatus provided with a carbon dioxide absorption tower and with a carbon dioxide-absorbing solution regenerating tower;

feeding the carbon dioxide thus recovered to the upstream side and/or the downstream side of the reformer;

allowing reaction of the synthesis gas to take place over a methanol-synthesizing catalyst to produce a reaction product;

recovering liquid crude methanol from the reaction product;

distilling the liquid crude methanol in a distillation apparatus provided with a pressure distillation tower and with an atmospheric distillation tower to separate it into refined methanol and waste water containing low boiling point organic compounds and high boiling point organic compounds;

wherein bottom liquid in a topping tower of the distillation apparatus is heated and introduced into the pressure distillation tower in the distillation step, and the heat of distilled liquid discharged from the top of the pressure distillation tower is utilized as a heat source for the carbon dioxide-absorbing solution regenerating tower and as a heat source for the atmospheric distillation tower.

In the method of manufacturing methanol according to the present invention, the synthesis gas should preferably be produced according to such a process that a mixed gas comprising hydrocarbons and carbon dioxide recovered by the carbon dioxide recovery apparatus from combustion exhaust gas discharged from the reformer is introduced into a moistening device to incorporate water vapor into the mixed gas, the resultant mixed gas being subsequently fed to the reformer to undergo the reforming reaction to produce the synthesis gas.

It is also preferable, in the method of manufacturing methanol according to the present invention, that a waste heat of hot synthesis gas produced in the reformer is utilized as a heat source for regenerating carbon dioxide-absorbing solution in the carbon dioxide-absorbing solution regenerating tower.

It is further preferable, in the method of manufacturing methanol according to the present invention, that a waste heat of hot synthesis gas produced in the reformer is utilized as a heat source in the distillation apparatus in the aforementioned distillation step.

It is further preferable, in the method of manufacturing methanol according to the present invention, that a waste heat of hot synthesis gas produced in the reformer is utilized in such a manner that it is used as a heat source in the pressure distillation tower, then as a heat source for heating the bottom liquid in the topping tower, which is designed to be introduced into the pressure distillation tower, thereafter as a heat source for regenerating the carbon dioxide-absorbing solution in the carbon dioxide-absorbing solution regenerating tower, and finally, as a heat source for heating a bottom-circulating liquid in the topping tower.

According to the present invention, there is also provided a method of manufacturing methanol comprising:

reacting hydrocarbons with water vapor in a reformer to thereby produce a synthesis gas containing hydrogen, carbon monoxide and carbon dioxide;

recovering carbon dioxide from combustion exhaust gas which has been discharged from the reformer by a carbon dioxide recovery apparatus provided with a carbon dioxide absorption tower and with a carbon dioxide-absorbing solution regenerating tower;

feeding the carbon dioxide thus recovered to the upstream side and/or the downstream side of the reformer;

allowing reaction of the synthesis gas to take place over a methanol-synthesizing catalyst to produce a reaction product;

recovering liquid crude methanol from the reaction product;

distilling the liquid crude methanol in a distillation apparatus provided with a pressure distillation tower and with an atmospheric distillation tower to separate it into refined methanol and waste water containing low boiling point organic compounds and high boiling point organic compounds;

wherein a waste heat of hot synthesis gas produced in the reformer is utilized in such a manner that it is used as a heat source in the pressure distillation tower, then as a heat source for heating the bottom liquid in a topping tower of the distillation apparatus, which is designed to be introduced into the pressure distillation tower, thereafter as a heat source for regenerating the carbon dioxide-absorbing solution in the carbon dioxide-absorbing solution regenerating tower, and finally, as a heat source for heating a bottom-circulating liquid in the topping tower.

In this method of manufacturing methanol according to the present invention also, the synthesis gas should preferably be produced according to such a process that a mixed gas comprising hydrocarbons and carbon dioxide recovered by the carbon dioxide recovery apparatus from combustion exhaust gas discharged from the reformer is introduced into a moistening device to thereby incorporate water vapor into the mixed gas, the resultant mixed gas being subsequently fed to the reformer to undergo the reforming reaction to produce the synthesis gas.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Next, the methods of manufacturing methanol according to the present invention will be explained with reference to drawings.

Figure 1:
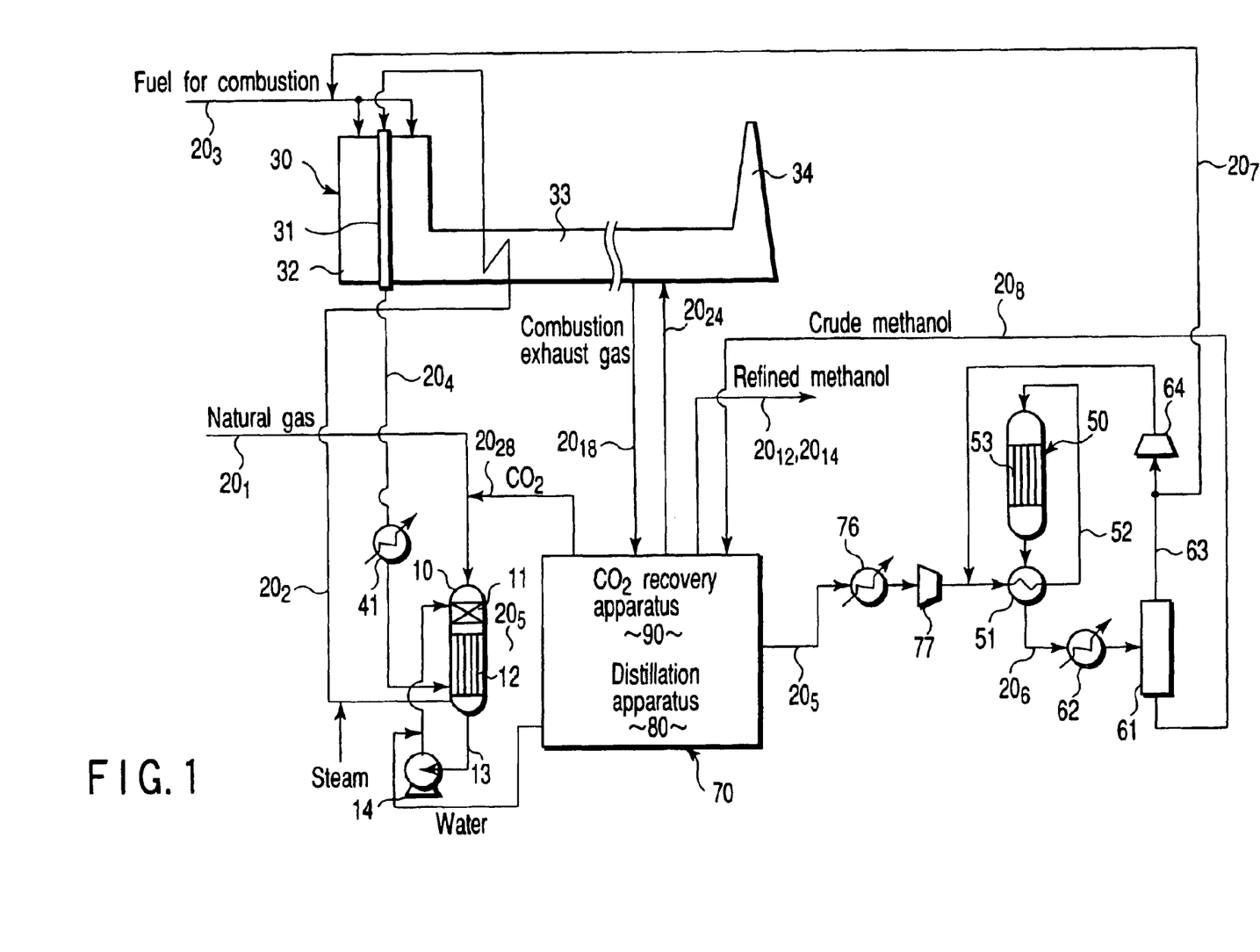
FIG. 1 is a flow chart schematically illustrating one example of the plant for manufacturing methanol according to the present invention.
Figure 2:
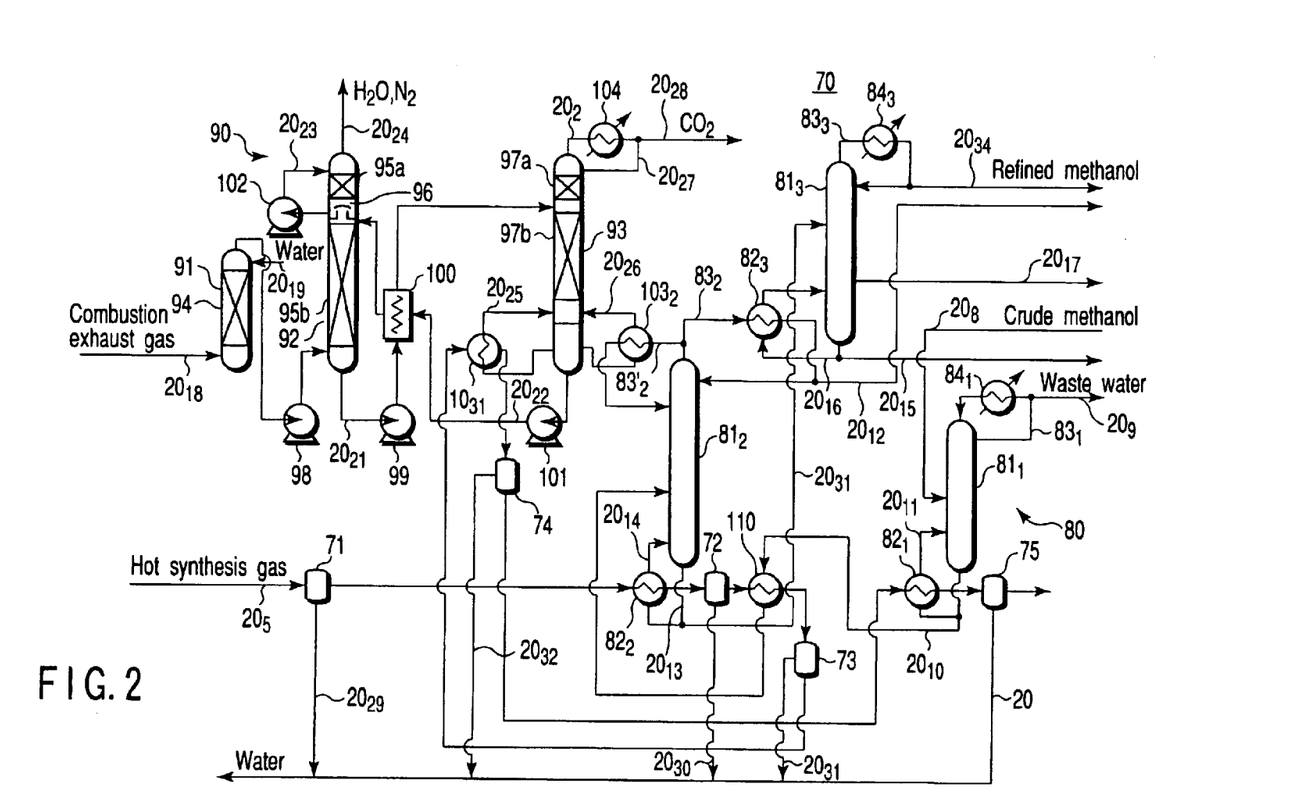
FIG. 2 is a flow chart schematically illustrating the carbon dioxide recovery/distillation apparatus which is designed to be incorporated into the methanol manufacturing plant shown in FIG. 1.

FIG. 1 schematically illustrates one example of the plant for manufacturing methanol; and FIG. 2 illustrates the carbon dioxide recovery apparatus employing a carbon dioxide-absorbing solution and the distillation apparatus of the methanol manufacturing plant shown in FIG. 1.

A moistening device, e.g. a single stage heat exchanger type moistening device 10 is provided therein with a filler layer 11 which is disposed close to the top of the moistening device 10, and with a tube 12 of wetted-wall type which is disposed below the filler layer 11 for contacting gas with water. A pump 14 for circulating water from the bottom of the moistening device 10 via a water circulating passageway 13 to the top of the moistening device 10 is disposed below the moistening device 10. A raw gas-feeding passageway $20_1$ is connected with the top of the moistening device 10. This raw gas-feeding passageway $20_1$ may be provided with a desulfurizing device (not shown).

A reformer 30 is disposed on the downstream side of the moistening device 10 and connected through a passageway $20_2$ with the moistening device 10. This reformer 30 is provided with a steam-reforming reaction tube 31, a combustion device 32 which is disposed to surround the reaction tube 31 so as to heat the reaction tube 31 through the combustion of a fuel, and a chimney 34 which is communicated through a convection portion (waste heat recovery portion) 33 with the combustion device 32. The reaction tube 31 is filled with a nickel-based catalyst. A fuel-feeding passageway $20_3$ is connected with the combustion device 32 of the reformer 30.

The reaction tube 31 of the reformer 30 is connected, via a passageway $20_4$ for passing a hot synthesis gas generated in the reaction tube 31, with the tube 12 of the moistening device 10. The passageway $20_4$ is provided with a heat exchanger 41. The moistening device 10 is connected through a passageway $20_5$ for passing hot synthesis gas with a methanol-synthesizing reaction apparatus 50. This reaction apparatus 50 is provided with a preheater 51 and also with a methanol synthesizing reactor 53 to which a synthesis gas is fed via a circulating passageway 52 from the preheater 51. This methanol synthesizing reactor 53 is filled with a methanol-synthesizing catalyst.

A gas-liquid separator 61 is connected through a passageway $20_6$ with the preheater 51. The passageway $20_6$ is provided with a cooler 62. The gas-liquid separator 61 is connected through a gas-circulating passageway 63 with a region of the passageway $20_5$ which is located close to the inlet of the preheater 51. The gas-circulating passageway 63 is provided with a gas compressor 64. A purge gas passageway $20_7$ is branched from a region of the gas-circulating passageway 63 which is located between the gas-liquid separator 61 and the gas compressor 64, and is connected with the fuel-feeding passageway $20_3$. The crude methanol that has been separated by the gas-liquid separator 61 is permitted to enter, via a passageway $20_8$, into a first distillation tower to be explained hereinafter.

The passageway $20_5$ is provided with various kinds of heat exchangers of the carbon dioxide recovery/distillation apparatus 70, and with a plurality of condensers, each disposed on the front and rear sides of each of these heat exchangers.

Namely, as shown in FIG. 2, the passageway $20_5$ is provided with a first condenser 71, a heat exchanger $82_2$ of a second distillation tower, i.e. a pressure distillation tower $81_2$ of distillation apparatus 80, a second condenser 72, a heat exchanger 110 for heating bottom liquid of a first distillation tower, i.e. a topping tower $81_1$, to be explained hereinafter, which is designed to be introduced into the heat exchanger $82_2$, a third condenser 73, a first regenerating tower heat exchanger $103_1$ of a carbon dioxide ($CO_2$) recovery apparatus 90, a fourth condenser 74, a heat exchanger $82_1$ of a first distillation tower $81_1$ of the distillation tower 80, and a fifth condenser 75, all of which are arranged in the mentioned order starting from the moistening device 10.

The first distillation tower $81_1$ is disposed on the downstream side of the gas-liquid separator 61 and connected via the passageway $20_8$ with the gas-liquid separator 61. A circulating passageway $83_1$ is connected with a top portion of the first distillation tower $81_1$ and provided with a first condenser $84_1$. By the way, a passageway $20_9$ for discharging impurities having a lower boiling point than methanol is branched from the circulating passageway $83_1$. The bottom of the first distillation tower $81_1$ is connected, via a passageway $20_{10}$ which is intersected with the heat exchanger 110, with the sidewall of the second distillation tower $81_2$. A first distillation-heating passageway $20_{11}$ is branched from a region of the passageway $20_{10}$ which is located close to the bottom of the first distillation tower $81_1$, and is connected via the heat exchanger $82_1$ with a lower portion of the first distillation tower $81_1$.

The second distillation tower $81_2$ is disposed on the downstream side of the first distillation tower $81_1$ and connected via the passageway $20_{10}$ with the first distillation tower $81_1$. A couple of circulating passageways $83_2$ and $83_2'$ are connected with a top portion of the second distillation tower $81_2$. By the way, the passageway $20_{12}$ for recovering refined methanol is branched from the circulating passageways $83_2$. A heat exchanger $82_3$ serving as a second condenser and also as a heat source for a third distillation tower, i.e. an atmospheric distillation tower $81_3$ is mounted on the circulating passageways $83_2$. A second regenerating tower heat exchanger $103_2$ of a carbon dioxide recovery apparatus 90 to be discussed hereinafter is mounted on the other circulating passageway $83_2'$. The bottom of the second distillation tower $81_2$ is connected through the passageway $20_{13}$ with the sidewall of the third distillation tower $81_3$. A second distillation tower-heating passageway $20_{14}$ is branched from a region of the passageway $20_{13}$ which is located close to the bottom of the second distillation tower $81_2$, and is connected via the heat exchanger $82_2$ with a lower portion of the second distillation tower $81_2$.

The third distillation tower $81_3$ is disposed on the downstream side of the second distillation tower $81_2$ and connected via the passageway $20_{13}$ with the second distillation tower $81_2$. A circulating passageway $83_3$ is connected with a top portion of the third distillation tower $81_3$ and is provided with a third condenser $84_3$. By the way, the passageway $20_{34}$ for recovering refined methanol is branched from the circulating passageways $83_3$. The bottom of the third distillation tower $81_3$ is connected with a waste water-discharging passageway $20_{15}$. A third distillation tower-heating passageway $20_{16}$ is branched from a portion of the waste water-discharging passageway $20_{15}$ which is located close to the bottom of the third distillation tower $81_3$, and is connected via the heat exchanger $82_3$ with a lower portion of the third distillation tower $81_3$. By the way, a side-cutting passageway $20_{17}$ is extended outside the system from the sidewall of the third distillation tower $81_3$.

The carbon dioxide recovery apparatus 90 is connected through a combustion exhaust gas-feeding passageway $20_{18}$ with the convection portion 33 of the reformer 30. This carbon dioxide recovery apparatus 90 is provided as shown in FIG. 2 with a cooling tower 91, a carbon dioxide absorption tower 92 and an absorbing liquid regenerating tower 93, all of which are arranged neighboring each other. The cooling tower 91 is provided therein with a gas-liquid contacting member 94. The carbon dioxide absorption tower 92 is provided therein with a couple of upper and lower gas-liquid contacting members 95a and 95b, between which an overflow portion 96 for a regenerated absorbing liquid is disposed. The absorbing liquid regenerating tower 93 is provided therein with a couple of upper and lower gas-liquid contacting members 97a and 97b.

The cooling tower 91 is connected via the combustion exhaust gas-feeding passageway $20_{18}$ with the convection portion 33. It is designed such that the cooling water can be sprayed onto an upper portion of the cooling tower 91 through a passageway $20_{19}$, and that the combustion exhaust gas that has been introduced through the combustion exhaust gas-feeding passageway $20_{18}$ into the cooling tower 91 is cooled by the gas-liquid contacting member 94. The top portion of the cooling tower 91 is connected via a passageway $20_{20}$ with a lower portion of the carbon dioxide absorption tower 92, and this passageway $20_{20}$ is provided with a blower 98. The bottom of the carbon dioxide absorption tower 92 is connected through a passageway $20_{21}$ with a sidewall portion of the absorbing liquid regenerating tower 93 which is located between the upper and lower gas-liquid contacting members 97a and 97b. A pump 99 and a heat exchanger 100 are successively mounted on the passageway $20_{21}$, the pump 99 being located closer to the carbon dioxide absorption tower 92 than the heat exchanger 100. The bottom of the absorbing liquid regenerating tower 93 is connected through a passageway $20_{22}$ with an upper portion of the carbon dioxide absorption tower 92 where an overflow portion 96 is located, the passageway $20_{22}$ being provided so as to pass through a heat exchanger 100. A pump 101 is mounted on a region of the passageway $20_{22}$ which is located between the bottom of the absorbing liquid regenerating tower 93 and the heat exchanger 100.

A passageway $20_{23}$ is communicated with the carbon dioxide absorption tower 92 in such a way that one end thereof is connected with the overflow portion 96 of the carbon dioxide absorption tower 92 and the other end thereof is connected via a pump 102 with a portion of the carbon dioxide absorption tower 92 which is located over the upper gas-liquid contacting member 95a. An exhaust passageway $20_{24}$ is connected, through one end thereof with a top portion of the carbon dioxide absorption tower 92, the other end thereof being connected with the convection portion 33 of the reformer 30. A couple of circulating passageways $20_{25}$ and $20_{26}$ are connected through their one ends with a lower portion of the absorbing liquid regenerating tower 93, the other end thereof being connected with a portion of the absorbing liquid regenerating tower 93 which is located immediately below the lower gas-liquid contacting member 97b. These circulating passageways $20_{25}$ and $20_{26}$ are arranged to intersect with the first and second regenerating tower heat exchangers $103_1$ and $103_2$, respectively. A circulating passageway $20_{27}$ is connected through one end thereof with a top portion of the absorbing liquid regenerating tower 93 and provided with a cooling heat exchanger 44. The passageway $20_{28}$ for passing recovered carbon dioxide therethrough is branched from the passageway $20_{27}$ and the distal end thereof is connected with the passageway $20_1$ for passing a raw gas. This passageway $20_{28}$ may be provided with a compressor fro compressing carbon dioxide passing therethrough.

By the way, a region of the passageway $20_5$ for passing the synthesis gas, which is located on the downstream side of the fifth condenser 75 is provided with a cooling heat exchanger 76 and a compressor 77.

Further, the first, second, third, fourth and fifth condensers 71–75 are connected, through passageways $20_{29}$–$20_{33}$, with the circulating water passageway 13 of the moistening device 10. Owing to this connecting system, the condensed water to be obtained in these condensers 71–75 can be fed to the moistening device 10 and utilized for humidifying the natural gas.

Next, a method of manufacturing methanol will be explained with reference to the methanol manufacturing plant shown in FIGS. 1 and 2.

1) Synthesis Gas Producing Step:

First of all, a fuel for combustion, e.g. natural gas is fed through the fuel feeding passageway $20_3$ to the combustion device 32 of the reformer 30. A portion of unreacted gas, i.e. purged gas mainly containing hydrogen which is generated from the gas-liquid separator 61 is fed, through the purge gas passageway $20_7$ and the fuel-feeding passageway $20_3$, to the combustion device 32 of the reformer 30. In this combustion device 32, the aforementioned natural gas and purge gas are allowed to combust together with air to thereby heat the interior of the reaction tube 31 up to a sufficiently high temperature, e.g. 850 to 900° C. The reason for heating the reaction tube 31 to such a high temperature is due to the fact that the reforming reaction inside the reformer 30 is an endothermic reaction. The combustion exhaust gas containing carbon dioxide that has been generated in the combustion device 32 is transferred through the convection portion 33 to the chimney 34. This combustion exhaust gas is cooled, as it passes through the convection portion 33, by the heat exchange thereof with a raw gas, e.g. natural gas passing through the raw gas-feeding passageway $20_1$ and mixed with steam as well as by the heat exchange thereof with boiler water (not shown).

The combustion exhaust gas cooled in the convection portion 33 is fed through the combustion exhaust gas-feeding passageway $20_{18}$ to the cooling tower 91 of the carbon dioxide recovery apparatus 90 shown in FIG. 2, and is further cooled at the gas-liquid contacting member 94 by cooling water which is fed through the passageway $20_{19}$. The combustion exhaust gas thus cooled is fed through the passageway $20_{20}$ to a lower portion of the carbon dioxide absorption tower 92 from a top portion of the cooling tower 91 by the actuation of the blower 98. During the period this combustion exhaust gas is being moved upward through the lower gas-liquid contacting member 95b disposed inside the carbon dioxide absorption tower 92, the carbon dioxide included in the combustion exhaust gas is permitted to contact with a regenerating absorbing liquid, e.g. a regenerating amine solution, that has been fed from the absorbing liquid regenerating tower 93 through the passageway $20_{22}$ (which passes through the heat exchanger 100) to the overflow portion 96 of the carbon dioxide absorption tower 92, thereby enabling the carbon dioxide to be absorbed by the amine solution. Further, during the period this combustion exhaust gas is being moved upward through the upper gas-liquid contacting member 95a after passing through the overflow portion 96, unabsorbed carbon dioxide remaining in the combustion exhaust gas is permitted to contact with a regenerating amine solution that has been fed through the passageway $20_{23}$ to a top portion of the carbon dioxide absorption tower 92 by the actuation of the pump 102, thereby enabling the unabsorbed carbon dioxide to be absorbed by the amine solution. The combustion exhaust gas thus eliminated of carbon dioxide is permitted to return, via the exhaust passageway $20_{24}$, to the convection portion 33 of the reformer 30 and discharged out of the system through the chimney 34.

The amine solution having carbon dioxide absorbed therein is stored at the bottom portion of the carbon dioxide absorption tower 92. The amine solution thus stored is enabled, by the actuation of the pump 99, to be fed therefrom and via the passageway $20_{21}$ to an upper portion of the absorbing liquid regenerating tower 93, which is located between a couple of the upper and lower gas-liquid contacting members 97a and 97b of the absorbing liquid regenerating tower 93. In this case, during the period this amine solution having carbon dioxide absorbed therein is being passed through the heat exchanger 100 mounted on the passageway $20_{21}$, the amine solution is heat-exchanged with a regenerated amine solution having a relatively high temperature and passing through the passageway $20_{22}$ which is connected with the bottom of the absorbing liquid regenerating tower 93, thereby heating up the amine solution and at the same time, cooling the regenerated amine solution passing through the passageway $20_{22}$ and having a relatively high temperature. The carbon dioxide-absorbed amine solution which has been heated up in this manner is then separated into carbon dioxide and regenerated amine solution during the period the amine solution flows down through the lower gas-liquid contacting member 97b of the heated absorbing liquid regenerating tower 93. On this occasion, the regenerated amine solution that has been stored in the bottom of the regenerating tower 93 is permitted to pass through a couple of circulating passageways $20_{25}$ and $20_{26}$ which are connected with a lower portion of the regenerating tower 93, during which the regenerated amine solution is heat-exchanged at the first regenerating tower heat exchanger $103_1$ which is mounted on the passageway $20_5$ through which a high-temperature synthesis gas is permitted to pass as explained hereinafter. The regenerated amine solution is heat-exchanged and heated at the second regenerating tower heat exchanger $103_2$ which is mounted on the circulating passageway $83_2$' through which a high-temperature distillation liquid is permitted to pass from the top of the second distillation tower $81_2$.

When the regenerating tower 93 is heated using the heated regenerated amine solution stored in the bottom of the regenerating tower 93 as a heat source, the carbon dioxide-absorbed amine solution is separated into carbon dioxide and a regenerated amine solution. The regenerated amine solution which has been separated in this manner is stored at the bottom of the regenerating tower 93 and then returned through the passageway $20_{22}$ to the carbon dioxide absorption tower 92 by the actuation of the pump 101. On the other hand, the carbon dioxide that has been separated from the carbon dioxide-absorbed amine solution is permitted to move up through the upper gas-liquid contacting member 97a of the regenerating tower 93 and circulated through the circulating passageway $20_{27}$ from a top portion of the absorbing liquid regenerating tower 93, during which the carbon dioxide is cooled by the cooling heat exchanger 104, thereby condensing the amine vapor which is being carried together the carbon dioxide, the condensed amine solution being subsequently permitted to return to the absorbing liquid regenerating tower 93. The carbon dioxide thus recovered is fed, through the passageway $20_{28}$ which is branched from the circulating passageway $20_{27}$, to the passageway $20_1$ disposed for passing natural gas.

As a raw gas, e.g. natural gas mainly consisted of hydrocarbons that have been desulfurized by a desulfurizer (not shown) passes through the raw gas-feeding passageway $20_1$, a predetermined quantity of carbon dioxide that has been recovered by the carbon dioxide recovery apparatus 90 is added, by way of the passageway $20_{28}$, to the raw gas and mixed therewith. This mixed gas comprising the natural gas and carbon dioxide is then transferred toward the filler layer 11 disposed at a top portion of the heat exchanger type moistening device 10. In this case, the pump 14 which is disposed below the heat exchanger type moistening device 10 is actuated in advance to thereby enable water to circulate from the bottom of the heat exchanger type moistening device 10 to the top portion of the heat exchanger type moistening device 10 through the circulating water passageway 13, thus moistening the mixed gas comprising the natural gas and carbon dioxide that has been introduced into the top portion of the heat exchanger type moistening device 10. After the mixed gas has been contacted with and moistening by the water that has been supplied from the circulating water passageway 13 at the filler layer 11, the mixed gas is further moistening through the heat exchange thereof at the tube 12 with a hot synthesis gas that has been supplied thereto from the reformer 30 through the passageway $20_4$. As a result, the mixed gas is substantially moistening with water vapor.

By the way, it is preferable, on the occasion of mixing the natural gas with carbon dioxide and steam, to set the mixing ratio of methane ($CH_4$) in the natural gas: steam ($H_2O$) to 1:1.5–1:5 (based on molar ratio), and the mixing ratio of methane ($CH_4$):carbon dioxide ($CO_2$) to 1:0.1—1:3 (based on molar ratio).

The natural gas incorporated with carbon dioxide and steam is permitted to pass through the passageway $20_2$ and then, heated during the period the natural gas is permitted to pass through the convection portion 33 of the reformer 30, after which the natural gas is fed to the reaction tube 31 which has been heated up to a sufficient temperature.

All of these steam, carbon dioxide and natural gas consisting mainly of methane ($CH_4$) that have been fed to the reaction tube 31 of the reformer 30 are allowed to react with each other in the presence of a catalyst in the reaction tube 31, wherein the steam-reforming of methane is allowed to take place, thus producing a hot synthesis gas comprising hydrogen, carbon monoxide and carbon dioxide according to the following formulas (1) and (2).

$$CH_4 + H_2O \rightleftarrows CO + 3H_2 \qquad (1)$$

$$CO + H_2O \rightleftarrows CO_2 + H_2 \qquad (2)$$

As seen from these formulas (1) and (2) of reforming reaction, as a result of the reaction between one mole of methane and two moles of steam, four moles of hydrogen and one mole of carbon dioxide are produced. In the actual reaction system however, a composition which is close to the chemical reaction equilibrium composition that will be determined by the outlet temperature and pressure of the reaction tube 11 can be obtained.

2) Heat Exchange and Cooling Step of Hot Synthesis Gas:

The hot synthesis gas produced at the reformer 30 is transferred via the passageway $20_4$ to the heat exchanger 41, wherein the hot synthesis gas is used for heating boiler water to generate a high-pressure steam, and at the same, the hot synthesis gas itself is cooled and then fed to an outer passageway of the tube 12 of the moistening device 10. In this tube 12, part of the heat of the synthesis gas is recovered and utilized as a heat source for the moistening device 10.

The synthesis gas passed through the moistening device 10 is fed via the passageway $20_5$ to the methanol-synthesizing reaction apparatus 50 as shown in FIG. 1. On this occasion, during the period this synthesis gas passes through the passageway $20_5$, this synthesis gas is cooled through the heat exchange thereof with the heat exchanger $82_2$ of the second distillation tower $81_2$, with the heat exchanger 110 disposed for heating the bottom liquid on the first distillation tower $81_1$ as the bottom liquid is introduced into the second distillation tower $81_2$, with the first regeneration tower heat exchanger $103_1$ of the carbon dioxide recovery apparatus 90, and with the heat exchanger $82_1$ of the first distillation tower $81_1$. The synthesis gas thus cooled is further cooled by the cooling heat exchanger 76 and then pressurized, by means of the compressor, up to a pressure, for example, 50–150 atm, which is suited for the methanol synthesizing reaction. Namely, the waste heat of the synthesis gas is effectively utilized during the processes the synthesis gas passes through the aforementioned heat exchangers, thus allowing synthesis gas itself to be cooled in these processes. Further, the water vapor included in the synthesis gas is turned into condensed water by the first, second, third, fourth and fifth condensers 71–75, the condensed water being fed, through passageways $20_{29}$–$20_{33}$, to the circulating water passageway 13 of the moistening device 10, thereby enabling the condensed water to be utilized in humidifying the raw gas that has been introduced into the moistening device 10.

3) Crude Methanol Synthesizing Step:

The synthesis gas pressurized is fed through the passageway $20_5$ to the preheater 51 of the methanol-synthesizing reaction apparatus 50, in which the synthesis gas is heated up to a temperature, e.g. 200–300° C., which is suited for the methanol synthesis reaction. Thereafter, the preheated synthesis gas is fed through the circulating passageway 52 to the reactor 53 which is filled with methanol synthesis catalyst. By the way, the unreacted gas which has been separated at the gas-liquid separator 61 to be explained hereinafter is fed through the gas circulating passageway 63 to a region of the passageway $20_5$ which is located immediately before the preheater 51, thereby enabling the unreacted gas to be mixed with the synthesis gas. In the reactor 53, a product containing methanol that has been synthesized according to the reactions as shown in the following formulas (3) and (4) can be obtained.

$$CO + 2H_2 \rightleftarrows CH_3OH \qquad (3)$$

$$CO_2 + 3H_2 \rightleftarrows CH_3OH + H_2O \qquad (4)$$

Furthermore, due to side reactions, impurities such as dimethyl ether and ethanol are produced. These impurities and water are existed together with methanol in the aforementioned product to form a liquid crude methanol.

4) Liquid Crude Methanol Recovering Step:

The product obtained from the reactor 53 is successively fed through the circulating passageway 52 and the passageway 20$_6$ to the cooler 62 so as to be cooled down to ordinary temperature. At this moment, most of the methanol and steam contained in the product are condensed and permitted to enter as a liquid into the gas-liquid separator 61. In this gas-liquid separator 61, the product is separated into liquid crude methanol and an unreacted gas, i.e. a hydrogen-rich unreacted gas mainly consisting of hydrogen.

Most of this hydrogen-rich unreacted gas is then fed through the gas circulating passageway 63 to the gas compressor 64, in which the hydrogen-rich unreacted gas is compressed and then circulated through the gas circulating passageway 63 to a region of the passageway 20$_5$ which is located at the inlet of the preheater 51 so as to be fed together with the synthesis gas to the reactor 53. Part of the hydrogen-rich unreacted gas is employed as a purge gas and passed through the purge gas passageway 20$_7$ and the fuel-introducing passageway 20$_3$ so as to be utilized as part of the fuel for the combustion device 32 in the reformer 30.

5) Distillation Step:

The liquid crude methanol which has been separated by the gas-liquid separator 61 is fed through the passageway 20$_8$ to the first distillation tower 81$_1$ of the distillation apparatus 80. In this first distillation tower 81$_1$, the bottom liquid mainly consisting of methanol and water is permitted to circulate the first distillation tower heating passageway 20$_{11}$ which is branched from the passageway 20$_{10}$, and is heated through the heat exchange thereof at the heat exchanger 82$_1$ which is intersected with the passageway 20$_5$ of the hot synthesis gas, thereby enabling the bottom liquid to be utilized as a heat source for the first distillation tower 81$_1$. In the top portion of the first distillation tower 81$_1$ which is heated in this manner, impurities having a lower boiling point than methanol are discharged out of the system by way of the passageway 20$_9$ which is branched from the circulating passageway 83$_1$ and part of the impurities is condensed by the first condenser 84$_1$ and refluxed by way of the circulating passageway 83$_1$.

The bottom liquid of the first distillation tower 81$_1$ is heated through the heat exchange thereof with the heat exchanger 110 intersecting with the passageway 20$_5$ of hot synthesis gas as the bottom liquid passes through the passageway 20$_{10}$, the heated bottom liquid being subsequently introduced into the second distillation tower 81$_2$. In this second distillation tower 81$_2$, this bottom liquid mainly consisting of methanol and water is permitted to circulate the second distillation tower heating passageway 20$_{14}$ which is branched from the passageway 20$_{13}$ and heated through the heat exchange thereof with the heat exchanger 82$_2$ intersecting with the passageway 20$_5$ of hot synthesis gas, thus enabling the heated bottom liquid to be utilized as a heat source for the second distillation tower 81$_2$. At the top portion of the second distillation tower 81$_2$ heated in this manner, this bottom liquid mainly consisting of methanol and water that has been supplied from the first distillation tower 81$_1$ is permitted to enter, as a distillation solution, into a couple of circulating passageways 83$_2$ and 83$_2$'. During the period this bottom liquid passes through these circulating passageways 83$_2$ and 83$_2$', this bottom liquid is cooled and condensed through the heat exchange thereof with the heat exchanger 82$_3$ mounted on the circulating passageway 83$_2$ and functioning not only as the second condenser but also as a heat source for the third distillation tower 81$_3$ and also with the second regenerating tower heat exchanger 103$_2$ of the carbon dioxide recovery apparatus 90 which is mounted on the circulating passageway 83'$_2$, the bottom liquid thus condensed being subsequently refluxed to obtain a refined and highly purified methanol. This refined methanol is then taken out the system by way of the passageway 20$_{12}$. The bottom liquid of the second distillation tower 81$_2$ is mainly consisted of methanol and water, but also contains a small quantity of high-boiling point organic compounds and organic acids, as well as a minute amount of inorganic matters originating from the apparatus, this bottom liquid being subsequently fed through passageway 20$_{13}$ to the third distillation tower 81$_3$.

In this third distillation tower 81$_3$, the bottom liquid which is waste water mainly consisting of water is permitted to circulate the third distillation tower heating passageway 20$_{16}$ which is branched from the discharging passageway 20$_{15}$ and heated through the heat exchange thereof with the heat exchanger 82$_3$ intersecting with the circulating passageway 83$_2$ of the distillation solution of the top portion of second distillation tower 81$_2$, thus enabling the heated bottom liquid to be utilized as a heat source for the third distillation tower 81$_3$. At the top portion of the third distillation tower 81$_3$ heated in this manner, this bottom liquid (mainly consisting of methanol and water) that has been supplied from the second distillation tower 81$_2$ is permitted to enter, as a distillation solution, into the circulating passageway 83$_3$. During the period this bottom liquid passes through the circulating passageway 83$_3$, this bottom liquid is cooled and condensed by the third condenser 84$_3$, the bottom liquid thus condensed being subsequently refluxed to obtain a refined and highly purified methanol. This refined methanol is then taken out the system by way of the passageway 20$_{34}$. A waste water mainly consisted of water, and also containing a small quantity of high-boiling point organic compounds and organic acids, as well as a minute amount of inorganic matters originating from the apparatus is stored at the bottom of the third distillation tower 81$_3$, this waste water being subsequently discharged through passageway 20$_{15}$ from the bottom of the third distillation tower 81$_3$.

As described above, according to the present invention, it is possible, through the addition of carbon dioxide together with hydrogen to a raw gas such as natural gas, to manufacture a synthesis gas having an $H_2/(CO+CO_2)$ ratio which is suited for synthesizing methanol. Further, since the combustion exhaust gas discharged from the reformer 30 is recovered by the carbon dioxide recovery apparatus 90 so as to utilize the carbon dioxide contained therein as a raw material for the manufacture of synthesis gas, the quantity of carbon dioxide to be discharged out of the system in the manufacture of synthesis gas can be reduced. As a result, the economy of methanol manufacturing plant can be improved particularly when the tax to the emission of carbon dioxide is newly introduced or when a more severe regulation for the emission of carbon dioxide is newly enforced.

Furthermore, the bottom liquid of the first distillation tower, i.e. topping tower 81$_1$ of the distillation apparatus 80 is heated by the heat exchanger 110 where the heat of hot synthesis gas is to be utilized prior to the feeding of the bottom liquid to the second distillation tower, i.e. pressure distillation tower 81$_2$, thereby making it possible to increase the quantity of distillation solution to be introduced into the circulating passageways 83$_2$ and 83$_2$' from the top of the second distillation tower 81$_2$. At the same time, the circulating passageway 83$_2$' is intersected and connected, through the second regenerating tower heat exchanger 103$_2$, with the circulating passageway $20_{26}$ of the absorption liquid-regenerating tower 93 of the carbon dioxide recovery apparatus 90, thereby making it possible to utilize the waste heat of the heated distillation solution as a heat source for the absorption liquid-regenerating tower 93. As a result, it is possible to reduce the total consumption of heat at the second and third distillation towers $81_2$ and $81_3$ as well as to he absorption liquid-regenerating tower 93 of the carbon dioxide recovery apparatus 90 as compared with the case where the distillation apparatus is disposed separate from the carbon dioxide recovery apparatus. Therefore, it is now possible to supply heat in conformity with any increase in heat source for the absorption liquid-regenerating tower 93, thereby making it possible to increase the production of methanol and to reduce the manufacturing cost of methanol.

Indeed, the case where the distillation apparatus is disposed separate from the carbon dioxide recovery apparatus (reference example) is compared with the case where the bottom liquid of the second distillation tower $81_1$ of the distillation apparatus 80 is preheated prior to the introduction thereof into the second distillation tower $81_2$, and the circulating passageway $83_2'$ of the second distillation tower $81_2$ is intersected and connected, through the second regenerating tower heat exchanger $103_2$, with the circulating passageway $20_{26}$ of the absorption liquid-regenerating tower 93 of the carbon dioxide recovery apparatus 90 (the present invention), thereby determining the ratio [a/b] of the amount of consumption of natural gas (fuel for the combustion) [a] per a unit quantity of production of methanol [b]. As a result, the ratio [a/b] in the present invention was 96 in comparison with the ratio [a/b] in the reference example which was assumed as being 100, thus indicating a lower fuel consumption, or a smaller heating energy, i.e. it was possible to supply heat in conformity with any increase in heat source for the absorption liquid-regenerating tower.

Further, since the waste heat of the hot synthesis gas generated in the reformer 30 is utilized as a heat source for the absorption liquid-regenerating tower 93 of the carbon dioxide recovery apparatus 90 and also as a heat source for the distillation apparatus 80, it becomes easier to supply heat in conformity with any increase in heat source for the absorption liquid-regenerating tower, thereby making it possible to increase the production of methanol and to reduce the manufacturing cost of methanol.

In particular, as shown in FIG. 2, the passageway $20_5$ through which a hot synthesis gas is designed to pass is provided, first of all, with the heat exchanger $82_2$ of the second distillation tower $81_2$ which is required to be heated at a highest temperature, with the heat exchanger 110 which is disposed on the downstream side of the heat exchanger $82_2$ and at a midway of the passageway through which the bottom liquid of the first distillation tower $81_1$ is introduced, with the first regenerating tower heat exchanger $103_1$ of the carbon dioxide recovery apparatus 90, and with the heat exchanger $82_1$ of the first distillation tower $81_1$, these heat exchangers being arranged in the mentioned order. Due to this arrangement, the waste heat of the hot synthesis gas can be utilized as a heat source of the second distillation tower $81_2$, then as a heat source for preheating the bottom liquid of the first distillation tower $81_1$ which is to be introduced into the second distillation tower $81_2$, further as a heat source for the regenerating tower 93 of the carbon dioxide recovery apparatus 90, and finally, as a heat source for the first distillation tower $81_1$.

Figure 3:
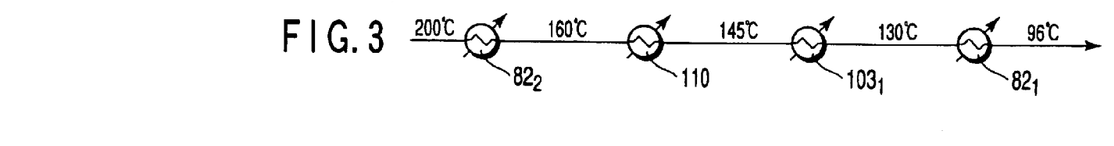
FIG. 3 is a diagram for illustrating changes in temperature on an occasion wherein a hot synthesis gas is successively heat-exchanged at a heat exchanger of a second distillation tower, at a heat exchanger disposed at a midway of the rout to feed bottom liquid of a first distillation tower to the second distillation tower disposed downstream, at a heat exchanger for a first regenerating tower of the carbon dioxide recovery apparatus, and at a heat exchanger for a first distillation tower, all of these heat exchangers being successively arranged in the mentioned order.

Changes in temperature on the occasion when a hot synthesis gas is permitted to pass through each of these heat exchangers $82_2$, 110, $103_1$ and $82_1$ are shown in FIG. 3. As clearly seen from this FIG. 3, the waste heat of hot synthesis gas can be more effectively utilized for the heating of the first and second distillation towers $81_1$ and $81_2$, for the preheating of the bottom liquid of the first distillation tower $81_1$ which is to be introduced into the second distillation tower $81_2$, and for the heating of the regenerating tower 93 of the carbon dioxide recovery apparatus 90. As a result, it becomes easier to supply heat in conformity with any increase in heat source for the absorption liquid-regenerating tower, thereby making it possible to further increase the production of methanol and to further reduce the manufacturing cost of methanol.

As described above, according to the present invention, it is possible to produce a synthesis gas having an $H_2/(CO+CO_2)$ molar ratio which is suited for the synthesis of methanol at the reformer. Further, since the heat of the distillation liquid recovered by the pressure distillation tower of the distillation apparatus can be utilized as a heat source for the absorption liquid-regenerating tower of the carbon dioxide recovery apparatus, it becomes easier to supply heat in conformity with any increase in heat quantity demanded in the carbon dioxide recovery apparatus, thereby making it possible to increase the production of methanol and to reduce the manufacturing cost of methanol.

Furthermore, according to the present invention, it is possible to produce a synthesis gas having an $H_2/(CO+CO_2)$ molar ratio which is suited for the synthesis of methanol at the reformer, and at the same time, since the heat of the distillation liquid recovered by the pressure distillation tower of the distillation apparatus can be utilized as a heat source for the carbon dioxide recovery apparatus, and since the waste heat of the hot synthesis gas produced in the reformer can be utilized as a heat source for the distillation apparatus, it becomes easier to supply heat in conformity with any increase in heat source demanded in the absorption liquid-regenerating tower, thereby making it possible to expect prominent effects such as a further increase in the production of methanol and a further reduction of the manufacturing cost of methanol.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing methanol comprising:
    reacting hydrocarbons with water vapor in a reformer to produce a synthesis gas containing hydrogen, carbon monoxide and carbon dioxide;
    recovering carbon dioxide from combustion exhaust gas which has been discharged from said reformer by a carbon dioxide recovery apparatus provided with a carbon dioxide absorption tower and with a carbon dioxide-absorbing solution regenerating tower;
    feeding the carbon dioxide thus recovered to the upstream side and/or the downstream side of said reformer;
    allowing reaction of the synthesis gas to take place over a methanol-synthesizing catalyst to produce a reaction product;
    recovering liquid crude methanol from the reaction product;
    distilling the liquid crude methanol in a distillation apparatus provided with a pressure distillation tower and with an atmospheric distillation tower to separate it into refined methanol and waste water containing low boiling point organic compounds and high boiling point organic compounds;

wherein bottom liquid in a topping tower of said distillation apparatus is heated and introduced into said pressure distillation tower in the distillation step, and the heat of distilled liquid discharged from the top of said pressure distillation tower is utilized as a heat source for said carbon dioxide-absorbing solution regenerating tower and as a heat source for said atmospheric distillation tower.

2. The method of manufacturing methanol according to claim 1, wherein the synthesis gas is produced according to a process wherein a mixed gas comprising hydrocarbons and carbon dioxide recovered by said carbon dioxide recovery apparatus from combustion exhaust gas discharged from said reformer is introduced into a moistening device to incorporate water vapor into the mixed gas, the resultant mixed gas being subsequently fed to said reformer to undergo the reforming reaction to produce the synthesis gas.

3. The method of manufacturing methanol according to claim 1 or 2, wherein said hydrocarbons are natural gas.

4. The method of manufacturing methanol according to claim 1, wherein a waste heat of hot synthesis gas produced in said reformer is utilized as a heat source for regenerating carbon dioxide-absorbing solution in said carbon dioxide-absorbing solution regenerating tower.

5. The method of manufacturing methanol according to claim 1, wherein a waste heat of hot synthesis gas produced in said reformer is utilized as a heat source in said distillation apparatus in said distillation step.

6. The method of manufacturing methanol according to claim 1, wherein a waste heat of hot synthesis gas produced in said reformer is utilized in such a manner that it is used as a heat source in said pressure distillation tower, then as a heat source for heating the bottom liquid in said topping tower, which is designed to be introduced into said pressure distillation tower, thereafter as a heat source for regenerating the carbon dioxide-absorbing solution in said carbon dioxide-absorbing solution regenerating tower, and finally, as a heat source for heating a bottom-circulating liquid in said topping tower.

7. A method of manufacturing methanol comprising:
reacting hydrocarbons with water vapor in a reformer to produce a synthesis gas containing hydrogen, carbon monoxide and carbon dioxide;
recovering carbon dioxide from combustion exhaust gas which has been discharged from said reformer by a carbon dioxide recovery apparatus provided with a carbon dioxide absorption tower and with a carbon dioxide-absorbing solution regenerating tower;
feeding the carbon dioxide thus recovered to the upstream side and/or the downstream side of said reformer;
allowing reaction of the synthesis gas to take place over a methanol-synthesizing catalyst to produce a reaction product;
recovering liquid crude methanol from the reaction product;
distilling the liquid crude methanol in a distillation apparatus provided with a pressure distillation tower and with an atmospheric distillation tower to separate it into refined methanol and waste water containing low boiling point organic compounds and high boiling point organic compounds;
wherein a waste heat of hot synthesis gas produced in said reformer is utilized in such a manner that it is used as a heat source in said pressure distillation tower, then as a heat source for heating the bottom liquid in a topping tower of said distillation apparatus, which is designed to be introduced into said pressure distillation tower, thereafter as a heat source for regenerating the carbon dioxide-absorbing solution in said carbon dioxide-absorbing solution regenerating tower, and finally, as a heat source for heating a bottom-circulating liquid in said topping tower.

8. The method of manufacturing methanol according to claim 7, wherein the synthesis gas is produced according to a process wherein a mixed gas comprising hydrocarbons and carbon dioxide recovered by said carbon dioxide recovery apparatus from combustion exhaust gas discharged from said reformer is introduced into a moistening device to incorporate water vapor into the mixed gas, the resultant mixed gas being subsequently fed to said reformer to undergo the reforming reaction to produce the synthesis gas.

9. The method of manufacturing methanol according to claim 7 or 8, wherein said hydrocarbons are natural gas.

* * * * *